US012629271B2

(12) United States Patent
Abad Belando

(10) Patent No.: US 12,629,271 B2
(45) Date of Patent: May 19, 2026

(54) DEVICE FOR INSERTING AN INFLATABLE INTRAGASTRIC BALLOON

(71) Applicant: Ramon Abad Belando, Barcelona (ES)

(72) Inventor: Ramon Abad Belando, Barcelona (ES)

(*) Notice: Subject to any disclaimer, the term of this patent is extended or adjusted under 35 U.S.C. 154(b) by 63 days.

(21) Appl. No.: 18/703,564

(22) PCT Filed: Oct. 19, 2022

(86) PCT No.: PCT/ES2022/070661
§ 371 (c)(1),
(2) Date: Apr. 22, 2024

(87) PCT Pub. No.: WO2023/073262
PCT Pub. Date: May 4, 2023

(65) Prior Publication Data
US 2024/0415680 A1      Dec. 19, 2024

(30) Foreign Application Priority Data

Oct. 25, 2021    (ES) ............................... ES202132088

(51) Int. Cl.
*A61F 5/00*          (2006.01)
(52) U.S. Cl.
CPC ............ *A61F 5/0036* (2013.01); *A61F 5/003* (2013.01)
(58) Field of Classification Search
CPC ...... A61F 5/0036; A61F 5/003; A61F 5/0089; A61F 5/0013; A61F 5/0069; A61F 5/0033; A61F 5/0079; A61F 2/958; A61F 2/0063; A61M 25/10; A61M 25/0668; A61M 25/02; A61M 2025/1093; A61M 2025/1054
USPC ............... 606/192, 191, 195; 604/96.01, 909
See application file for complete search history.

(56) References Cited

U.S. PATENT DOCUMENTS

| | | | | |
|---|---|---|---|---|
| 5,868,707 A | * | 2/1999 | Williams | .......... A61M 25/1029 604/103 |
| 6,355,013 B1 | * | 3/2002 | van Muiden | ......... A61M 25/10 604/164.05 |
| 2017/0290694 A1 | * | 10/2017 | Abad Belando | ...... A61F 5/0089 |

FOREIGN PATENT DOCUMENTS

| | | |
|---|---|---|
| WO | WO 2012/089881 | 7/2012 |
| WO | WO 2016/046427 | 3/2016 |

OTHER PUBLICATIONS

International Search Report issued in International Application No. PCT/ES2022/070661, mailed on Jan. 25, 2023.

* cited by examiner

*Primary Examiner* — Dianne Dornbusch
(74) *Attorney, Agent, or Firm* — Knobbe, Martens, Olson & Bear, LLP

(57)          ABSTRACT

A device is for inserting an inflatable intragastric balloon of the type that uses a filament for guidance. The device includes a first through channel from a proximal end to a distal end of the device through which the guiding filament for the device is inserted. The distal end has a flexible distal piece through which the first internal channel passes. An internal compartment is arranged adjacent and proximal with respect to the distal end and adjacent to a medial area of the device. An inflatable balloon is housed in the compartment. The compartment includes a flexible external membrane surrounding the balloon. A second through channel from the proximal end to the internal compartment is connected to a balloon arranged inside the internal compartment. The flexible external membrane is secured to the flexible distal piece and to the medial area of the device.

18 Claims, 5 Drawing Sheets

DEVICE FOR INSERTING AN INFLATABLE INTRAGASTRIC BALLOON

BACKGROUND

Field

The present invention relates to a device for inserting an inflatable intragastric balloon used for the treatment of obesity.

Description of the Related Art

In particular, the present invention relates to a device that allows an inflatable balloon (also known as a "gastric balloon") to be implanted temporarily in the stomach of obese patients and that helps to achieve significant weight loss in a short period of time.

The mid-90s of the last century saw the introduction of intragastric balloon treatment, offering an attractive option for weight loss in patients who did not respond to medical therapy and who did not want to or should not undergo surgery or pharmacological treatment.

This treatment comprises the use of a collapsed inflatable balloon attached to the distal end of a balloon inflation or feed tube that is blindly introduced through the patient's oral route and passes through the esophageal tract until it reaches the stomach. The balloon inflation tube must be long enough that the proximal end of said inflation tube stays outside the patient while the distal end penetrates the stomach. Once the collapsed balloon is inside the stomach, a syringe is inserted through the hole at the proximal end of said inflation tube protruding from the patient's mouth and a liquid or air is introduced, inflating the balloon inside the stomach. Once the balloon is inflated inside the stomach, the inflated balloon is released from the distal end of said inflation tube and said inflation tube is subsequently removed from inside the patient.

It is important to avoid oropharyngeal, laryngeal or tracheal injuries during intragastric balloon placement. In some cases, to avoid incorrect insertion of the balloon via the tracheal route, the patient is intubated beforehand through the patient's trachea using a respiratory tube to ensure the airway, and the balloon attached to the inflation tube is then inserted. However, the use of a respiratory tube requires control in addition to the control necessary for the insertion of the balloon, causes subsequent discomfort to the patient and does not ensure correct insertion of the balloon into the patient's stomach avoiding injury.

An example of a device for inserting a gastric balloon is disclosed in the PCT patent application published as WO 2012/089881. Said application discloses a device that is made up of a guide tube with a conical distal end attached adjacent to the inflation tube which in turn is attached to an inflatable balloon. The guide tube comprises an internal through hole from the proximal end to the distal end that allows the introduction of a preguiding filament. The latter is inserted beforehand into the patient's stomach and acts as a pathway via which the guide tube is introduced together with the inflation tube and the inflatable balloon into the stomach.

Additionally, in this type of device that comprises a preguiding filament that serves as a way of introducing the device and that is initially introduced through the patient's esophagus in an initial step, due to the flexible structure of said filament, it often becomes bent in the wall of the esophagus. When this happens, and the doctor subsequently introduces the guide tube into the patient via said filament, the conical distal end of said guide tube usually gets stuck at the point on said wall where said preguiding filament is bent, possibly causing serious injury to the wall of the esophagus and even causing a perforation of said wall, especially in patients with diverticula along this route.

Moreover, both in this type of device and in other prior art devices for inserting a gastric balloon, the procedure for releasing the inflated balloon inside the stomach is usually carried out with the aid of the anatomical structure of the cardia (the part of the stomach attached to the esophagus). When the inflation tube is pulled out of the patient, the cardia acts as a stop for the inflated balloon, severing the connection between the inflation tube and the inflated balloon, leaving the latter loose inside the stomach. However, in many cases, this habitual practice causes serious damage and injury to the cardia that, especially in obese patients and above all in some cases of morbid obesity, can cause internal bleeding that is difficult to deal with or even irreparable injury, especially in patients with a hiatal hernia.

The PCT patent application published as WO2016046427 discloses a device for inserting an inflatable balloon of the type that uses a filament to guide same, characterized in that it comprises a main body of revolution that defines a conical distal end and a proximal end, said main body further comprising:

- a first internal through channel from the proximal end to the distal end of said body for the insertion of a filament for guiding said device;
- an internal compartment arranged in a part of the distal end of said body for housing an inflatable balloon, said compartment comprising an external surface that is tearable and continuous with the surface of said body,
- a second internal through channel from the proximal end of said body to said compartment, for housing a balloon inflation tube, said inflation tube being adapted to be connected at its distal end to an inflatable balloon inside said compartment, and
- a distal end of said body ending in a head with a flexible neck through which said first internal channel is extended.

The distal structure of this device prevents the device from making undesired diversions toward other structures, reducing the risk of perforation and internal bleeding of the oropharynx, of the respiratory tract or injuries to the esophagus or cardia. Moreover, said device is bulky and can cause discomfort in patients with a narrow pharynx, esophagus and/or stomach, and can even cause significant injury to same in such patients.

Likewise, insertion devices are known in which the balloon is located in the most distal part of the device and is surrounded by a cylindrical membrane in the form of a prepuce, attached to the device at its most proximal end and open at its most distal end.

All prior art devices that have a compartment with a membrane have the problem that inflation of the balloon can sometimes cause the membrane or breakable surface surrounding the balloon to tear, leaving pieces of plastic inside the patient's stomach.

SUMMARY

It is an aim of the present invention to disclose a device that solves the aforementioned problems.

More specifically, the present invention discloses a device for inserting an inflatable intragastric balloon of the type that uses a filament to guide same, characterized in that it comprises:

a first through channel from a proximal end to a distal end of said device, for the insertion of the guiding filament for said device;

said distal end having a flexible distal piece through which said first internal channel passes an internal compartment arranged adjacent and proximal with respect to said distal end and adjacent to a medial area of the device, an inflatable balloon being housed in said compartment, said compartment comprising a flexible external membrane surrounding said balloon;

a second through channel from the proximal end to said internal compartment of the device, said second channel being connected to a balloon arranged inside said internal compartment, and in which said flexible external membrane is secured to said flexible distal piece and to the medial area of the device, said flexible membrane having a tear or pre-tear line to facilitate the emergence of the balloon during its inflation.

The existence of a tear line (or alternatively a pre-tear line) ensures that the balloon will emerge via the tear line as it inflates. Moreover, since the flexible membrane is attached to both the distal piece and the medial part of the device, this prevents parts of the membrane from becoming detached or not being attached to the insertion device. More specifically, the tear or pre-tear line may divide the flexible membrane into two parts, each one being attached, respectively, to a different part of the device. It is especially preferred that the tear line correspond to an area in which the material constituting the flexible membrane does not exist or disappears. This minimizes the likelihood of uncontrolled tearing of the membrane since, as the membrane already has a tear, the balloon, during its inflation, only needs to cause retraction of the two parts of the membrane in order to emerge from the compartment, without the need to rupture said membrane.

To maximize this effect, preferably, said tear or pre-tear line may be a closed line that divides the flexible membrane into two parts: a medial part secured to the medial area and a distal part secured to the flexible distal piece. This feature also facilitates the retraction of the membrane during the inflation process and prevents uncontrolled tearing of same. More preferably, said medial part of the flexible membrane is only attached to the medial area. Also more preferably, said distal part of the flexible membrane is only attached to the distal piece. Even more preferably, said tear line will be a line perpendicular to the main axis of the device.

Preferably, the compartment separates the distal piece and the medial area of the device, being interposed between the two. Even more preferably, the flexible membrane forms the lateral surface of the compartment in its entirety. This facilitates the emergence of the balloon, since it does not come up against non-flexible walls as it inflates.

Preferably, the medial area of the device has a medial piece that receives said first and second channels. More preferably, the flexible membrane is adhered to the distal piece and to the medial piece of the device.

Preferably, the first channel runs through the compartment. More preferably, the inflatable balloon is arranged, inside the compartment, wound around the first channel. This makes it easier for the balloon to exert more even pressure against the flexible membrane during the inflation process.

Preferably, the first channel runs through a first tube. Also preferably, the second channel runs through a second tube. More preferably, the two first and second tubes are connected to one another up to the medial area.

Preferably, the second channel ends in an inflation piece that connects the inflatable intragastric balloon to said second channel.

Preferably, the distal piece is a flexible piece with a generally conical shape ending in a blunt head. More preferably, said head has the shape of an ogive with a rounded tip.

BRIEF DESCRIPTION OF THE DRAWINGS

For a clearer understanding, several figures describing the various parts of a preferred embodiment of the present invention are attached by way of explanatory but non limiting example.

DETAILED DESCRIPTION

Figure 1:
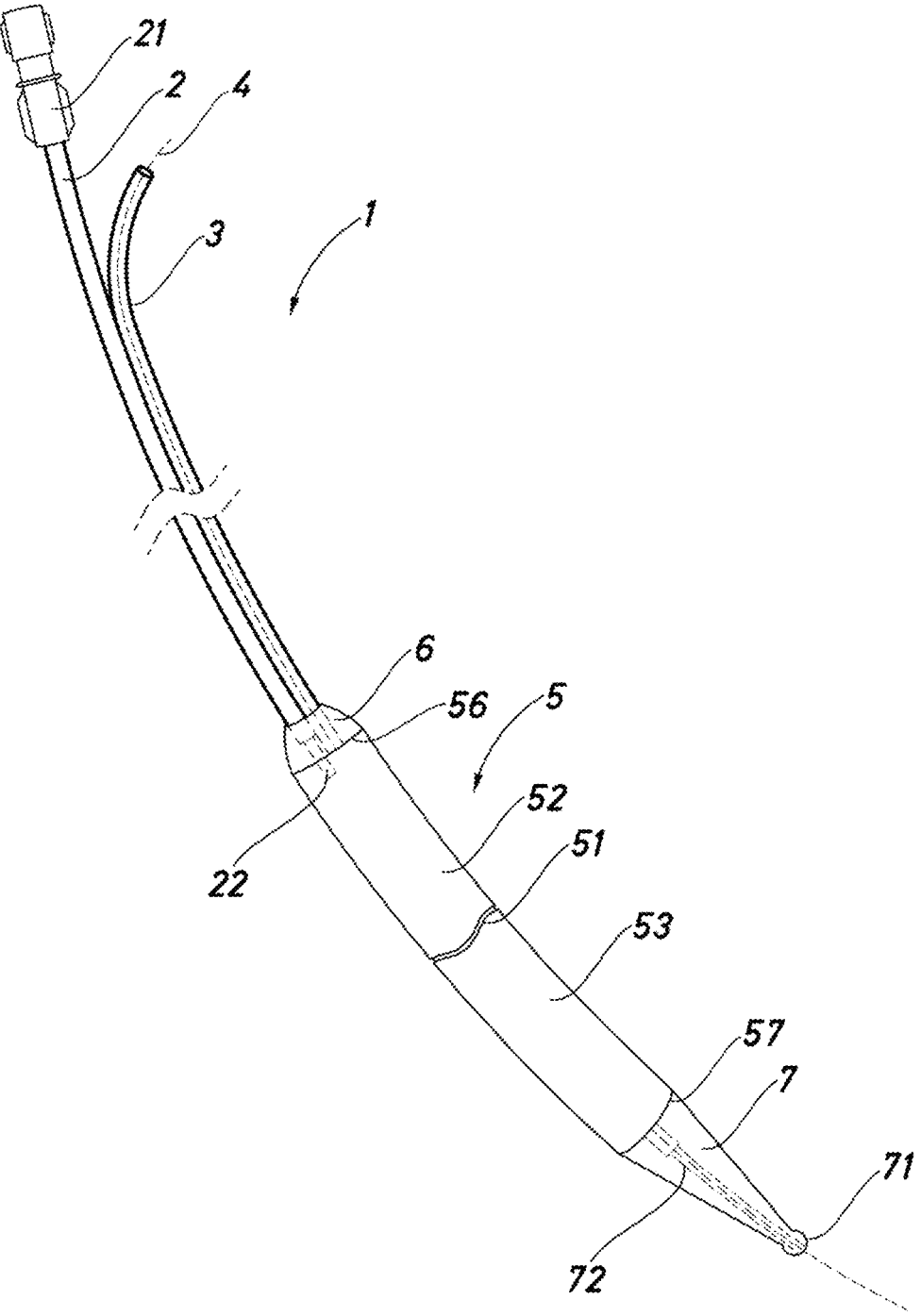
FIG. 1 shows a perspective view of an inflatable balloon insertion device.
Figure 2:
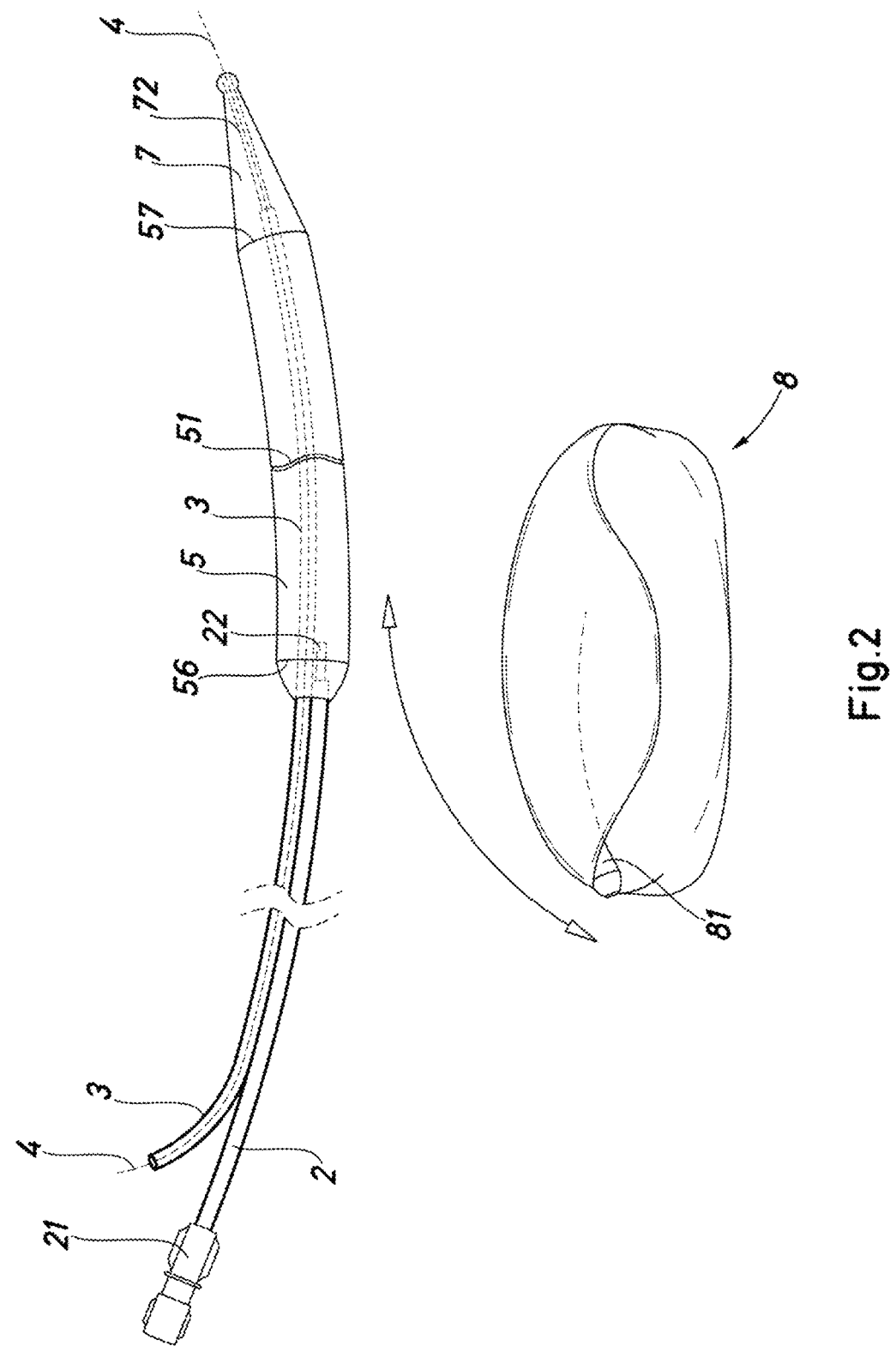
FIG. 2 shows another perspective view of the device, the inflatable balloon being shown collapsed, outside the device.

FIGS. 1 and 2 show a device 1 for inserting an inflatable balloon (also known as a "gastric balloon" or "intragastric balloon"). As can be seen, since it is intended to be inserted through the esophagus and into the stomach, it has a generally elongate shape, with a main axis, longitudinal axis or axial axis.

The device 1 comprises two tubes 2, 3. A first tube 3 the interior of which constitutes a first through channel from a proximal end to a distal end of the device. A guiding filament 4 (shown as a broken line in the figures) may run through said first channel. During placement of the gastric balloon in a patient's stomach, the guiding filament 4 is first inserted into the patient's stomach. Subsequently, the device is inserted in such a way that it is guided by the guiding filament 4. For this reason, the guiding filament 4 is sometimes referred to as a "preguiding filament".

The second tube 2 constitutes a second channel from the proximal end to a compartment in which the inflatable balloon 8 is located. The second tube 2 is used to inflate the balloon. In the example according to FIGS. 1 and 2, the second tube 2 ends in an inflation piece 21 intended to be inserted in a valve 81 for inflation of the balloon. The inflation piece 21 may simply be a tube made of material that is more rigid than the second tube 2 and the balloon 8. It could also be an inflation valve. The two tubes 2, 3 are approximately parallel to—or coincident with—the main or longitudinal axis of the device.

The two tubes 2, 3 are joined to one another up to the medial area of the device, for example by gluing via a generatrix. Other ways of joining are also possible. Alternatively, the two tubes could be not joined to one another. In another possible embodiment, the first and second channels correspond to two through holes belonging to a single body.

The device 1 has a medial area located between the distal and proximal ends. The medial area is located adjacent to the compartment in which the inflatable balloon is located, on the proximal side. In the example shown, the medial area has a medial piece 6 that receives the tubes 2, 3, allowing them to pass through it.

The distal end of the device 1 has a distal piece 7 which is preferably made of a flexible material. The distal piece 7 has a through hole 72 that is constituted as an extension of the first channel constituted by the first tube 3. The distal piece 7 of the example has the shape of an ogive with a rounded tip. More specifically, in the example, the distal piece 7 has a conical body with a rounded tip that has the shape of a blunt spherical head 71. In general, it is advantageous if the distal end of the distal piece 7 is thinner and more flexible than the proximal end of the distal piece 7. Thus, in the event that the preguiding filament possibly becomes bent at some point in the wall of the esophagus, the head in the shape of an ogive with a rounded tip allows the device to be redirected, avoiding damage and/or perforations in the wall of the esophagus and walls of other anatomical organs in the path of the device, such as, for example, the walls of the oropharynx and stomach.

As stated above, the device comprises an internal compartment inside which an inflatable balloon is housed. This compartment is arranged adjacent to said distal piece 7 and on the proximal side of said piece. Said compartment is also adjacent to the medial piece 6. The second inflation tube 2 is attached to the inflatable balloon 8 by means of a detachable connection. The inflation balloon 8 comprises an inflation valve 81 which is connected to the second tube 2, for its inflation (shown in FIG. 2), through the inflation piece 21. Due to its shape and function, the second tube 2 may also be referred to as a "balloon feed tube". The balloon inflation valve 81 prevents the balloon from deflating once it is fitted in a patient's stomach. The compartment is delimited by a flexible membrane 5, which is secured to the distal piece 7 and to the medial piece 6, surrounding the compartment. In the example, the connection lines 56, 57 for connection to the medial piece 6 and the distal piece 7, respectively, correspond to perimeter lines. This ensures that the membrane 5 surrounds the compartment for the inflatable balloon 8. The membrane 5 may be attached to the medial piece 6 and distal piece 7 by adhesion, fusion or any other method that is appropriate depending on the materials and the application. The first tube 3, or guide channel, passes through the compartment. The balloon 8 is placed inside the compartment, wound around the first tube 3 and/or surrounding the latter. To this end, the first tube 3 is preferably arranged along the axial axis of the compartment.

As can be seen, the distal piece 7 and the medial piece 6 are independent pieces, with no continuity between them, since the compartment separates the two pieces.

The flexible membrane 5 completely surrounds the inflatable balloon 8, constituting the entire side walls of the compartment. The flexible membrane 5 has a tear line 51 that divides the membrane 5 into two independent parts 52, 53. At said tear line, preferably, the material 5 of the membrane disappears completely, as can be seen in FIG. 1. The tear line 51 has a perimeter path, in such a way that it divides the membrane 5 into two parts, each one secured to a different area: a part 52 secured to the medial area and another part 53 secured to the distal area of the device. This arrangement of the membrane of the device will promote subsequent retraction of the independent parts 52, 53 of the membrane. To further facilitate this effect, the tear line extends in a plane approximately perpendicular to the axial axis of the compartment, and/or parallel to the distal and medial pieces. Alternatively, the tear line could extend, for example, along a generatrix, although it is believed that the perimeter path better promotes orderly emergence of the balloon during and after its inflation. The tear line 51 could be replaced by a pre-tear line, which could consist of a line of reduced membrane thickness or a line with discontinuous cuts, in such a way that when the balloon 8 is inflated inside the compartment, this will cause controlled tearing of the membrane 5 along the aforementioned pre-tear line.

The device may additionally comprise a length marking (not shown in the figures) for indicating the location of the head 71 of the device and the compartment in which the inflatable balloon is housed during the insertion of the device into the patient. This marking may be located, for example, on the proximal part of the first or second tube, or, alternatively, on a piece comprising both the first and second channels.

Figure 3:
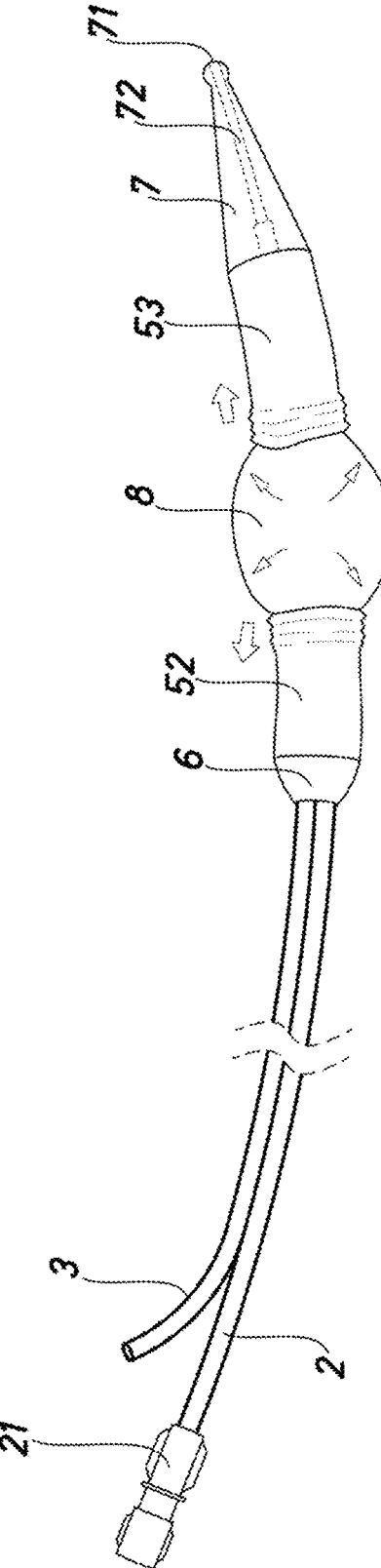
FIG. 3 shows a perspective view of the device, in a first inflation phase.
Figure 4:
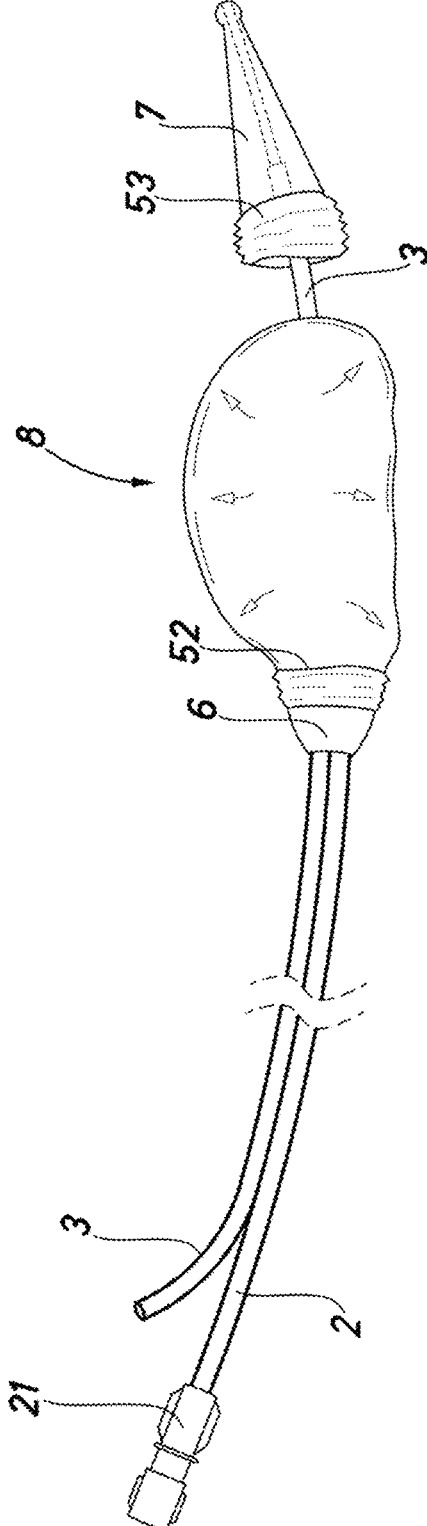
FIG. 4 shows a perspective view of the device, in a second inflation phase.
Figure 5:
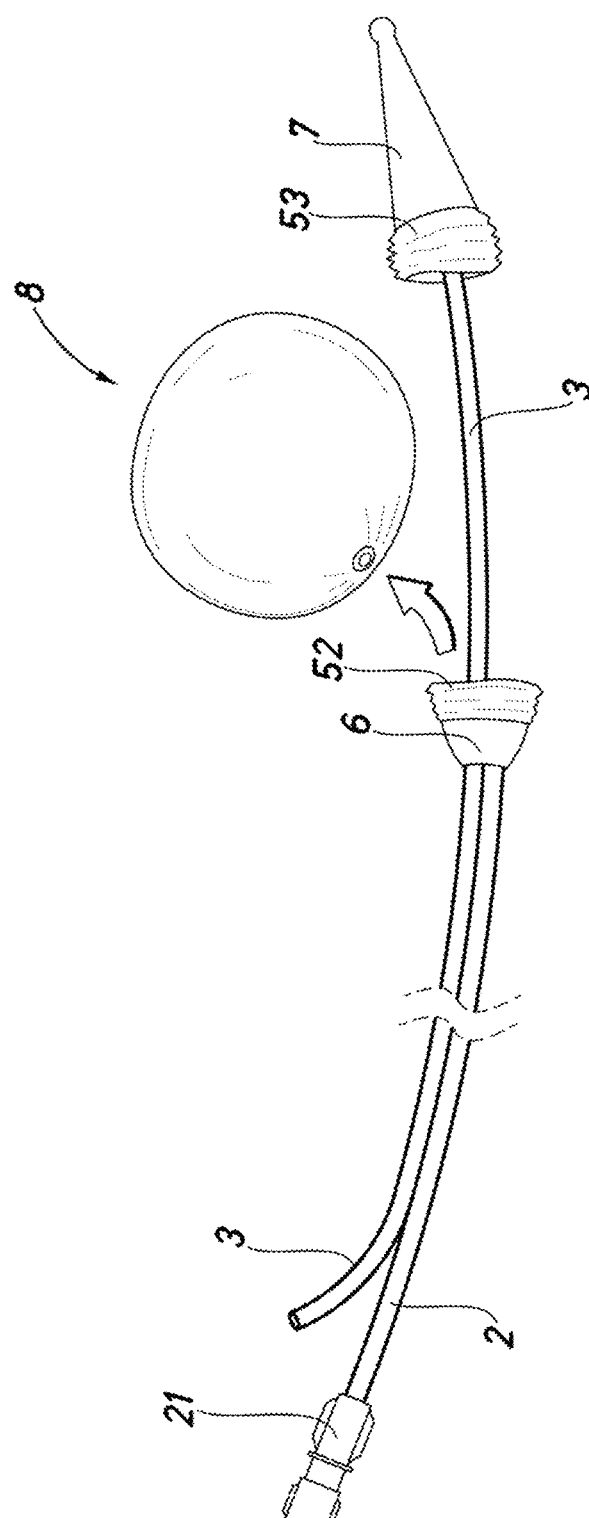
FIG. 5 shows a perspective view of the device, in a final placement phase, after inflation of the balloon, and its disconnection or release from the device.

FIGS. 3 to 5 show a method for inflating and releasing a balloon. Elements which are the same as or equivalent to those shown in the previous figures have been identified using identical numerals and, therefore, will not be described in depth. Note that in FIG. 4 an independent part 53 of the membrane has been shown more retracted than normal, to allow the guide tube 3 to be seen. In reality, said part 53 will normally be in contact with the balloon 8, since it is the latter that causes it to retract.

Note also that this method shown in FIGS. 3 to 5 is performed after inserting the device into the stomach of a patient, according to known techniques, and therefore, for the sake of clarity, the stomach or other organs of the patient have not been drawn. More specifically, the compartment must be located entirely within the stomach. For the sake of clarity, the guiding filament, which may remain in position during the method, is also not shown in the figure. An insertion method is described in documents WO2012089881 and WO2016046427.

To inflate the balloon 8, an inflation gas or liquid is introduced through the second tube 2, via the inflation head 21. The balloon 8, which is initially collapsed and surrounding the first tube, inflates upon receiving the inflation gas or liquid. This causes the dimensions of the balloon 8 to exceed those of the compartment, as shown in FIGS. 3 and 4. Consequently, the balloon begins to emerge through the tear line, optionally tearing same when the tear line is a pre-tear line and then separating the independent parts 52, 53 created by the tearing along the pre-tear line or directly causing the retraction of the two independent parts 52, 53 in the event that a tear line is provided from the start. As each independent part 52, 53 is attached to the medial piece 6 or to the distal piece 7, respectively, this prevents parts of the membrane from becoming detached and remaining loose inside the patient's stomach. As can be seen, the fact that the tear or pre-tear line 51 is perpendicular to the axial axis of the device 1 and/or of the compartment, together with the double attachment of the membrane to the distal and medial areas of the device, facilitates the retraction of the membrane and prevents uncontrolled tearing thereof and/or the release or detachment of portions of membrane in the stomach.

Once inflation is complete, the balloon 8 is released. Release may be achieved by the inflation pressure itself, by a specific movement, by a combination of both, or by any other method. Once the balloon 8 has been released in the stomach, the device 1 may be extracted without leaving anything other than the inflated balloon inside the patient's stomach. Subsequently, upon extraction of the device 1 from inside the patient, said device extracts the preguiding filament, the placement procedure thus being complete.

Therefore, the present invention allows, with a single compact device, the insertion of an inflatable balloon inside the stomach of a patient without complications, injuries or damage of any kind, eliminating the risk of perforations and/or bleeding of the airways, oropharynx, esophagus, stomach, and duodenum. Moreover, with the device according to the present invention, an efficient, fast (taking a few seconds) inflatable balloon insertion method is achieved, without the need for anesthesia and without the need for the intervention of any medical assistant, nurse and/or auxiliary. It also avoids detachment or release of loose portions of membrane that would remain inside the patient's stomach.

Although the invention has been described with respect to a preferred embodiment, this should not be considered as limiting the invention, the scope of which is defined by the broadest interpretation of the following claims.

What is claimed is:

1. A device for inserting an inflatable intragastric balloon of the type that uses a filament to guide same, comprising:
    a first through channel extending from a proximal end to a distal end of said device, for the insertion of the guiding filament for said device, wherein said distal end having a flexible distal piece through which said first through channel passes;
    an internal compartment arranged adjacent and proximal with respect to said distal end and adjacent to a medial area of the device, an inflatable balloon being housed in said internal compartment, said internal compartment comprising a flexible external membrane surrounding said inflatable balloon; and
    a second through channel extending from the proximal end to said internal compartment, said second through channel being connected to the inflatable balloon arranged inside said internal compartment,
    wherein said flexible external membrane is secured to said flexible distal piece and to the medial area of the device, said flexible external membrane having a tear or pre-tear line to facilitate the emergence of the inflatable balloon during its inflation.

2. The device of claim 1, wherein said tear or pre-tear line is a closed line that divides the flexible external membrane into two parts: a medial part secured to the medial area and a distal part secured to the flexible distal piece.

3. The device of claim 2, wherein said medial part of the flexible external membrane is only attached to the medial area.

4. The device of claim 2, wherein said distal part of the flexible external membrane is only attached to the distal piece.

5. The device of claim 1, wherein said tear line is a line perpendicular to a main axis of the device.

6. The device of claim 1, wherein the internal compartment separates the flexible distal piece and the medial area, being interposed between the two.

7. The device of claim 1, wherein the flexible external membrane forms a lateral surface of the compartment in its entirety.

8. The device of claim 1, wherein the tear line corresponds to an area in which a material constituting the flexible external membrane disappears.

9. The device of claim 1, wherein the medial area has a medial piece that receives said first and second through channels.

10. The device of claim 9, wherein the flexible external membrane is adhered to the flexible distal piece and to the medial piece.

11. The device of claim 1, wherein the first through channel runs through the internal compartment.

12. The device of claim 1, wherein the inflatable balloon is arranged, inside the internal compartment, wound around the first through channel.

13. The device of claim 1, wherein the second through channel ends in an inflation piece that connects the inflatable balloon to said second through channel.

14. The device of claim 1, wherein the first through channel runs through a first tube.

15. The device of claim 14, wherein the second through channel runs through a second tube.

16. The device of claim 15, wherein the two first and second tubes are connected to one another up to the medial area.

17. The device of claim 1, wherein the flexible distal piece is a flexible piece with a generally conical shape ending in a blunt head.

18. The device of claim 17, wherein said blunt head has the shape of an ogive with a rounded tip.

* * * * *